(12) United States Patent
Ezenwa

(10) Patent No.: US 7,179,231 B2
(45) Date of Patent: Feb. 20, 2007

(54) APPARATUS AND METHOD FOR ANALYZING NERVE CONDUCTION

(75) Inventor: Bertram N. Ezenwa, Mequon, WI (US)

(73) Assignee: Wisys Technology Foundation, Inc., Madison, WI (US)

( * ) Notice: Subject to any disclaimer, the term of this patent is extended or adjusted under 35 U.S.C. 154(b) by 410 days.

(21) Appl. No.: 10/647,495

(22) Filed: Aug. 25, 2003

(65) Prior Publication Data

US 2005/0049519 A1    Mar. 3, 2005

(51) Int. Cl.
*A61B 5/05* (2006.01)
*A61B 5/103* (2006.01)

(52) U.S. Cl. ...................... 600/554; 600/587
(58) Field of Classification Search ............. 600/372, 600/382, 384, 386, 390, 546, 547, 554, 587
See application file for complete search history.

(56) References Cited

U.S. PATENT DOCUMENTS

| | | | | |
|---|---|---|---|---|
| 3,067,749 A * | 12/1962 | Walters | ...................... | 600/384 |
| 4,526,169 A * | 7/1985 | Narishige et al. | ........... | 606/130 |
| 4,711,248 A * | 12/1987 | Steuer et al. | ............... | 600/561 |
| 5,215,100 A * | 6/1993 | Spitz et al. | .................. | 600/554 |
| 5,327,902 A * | 7/1994 | Lemmen | ..................... | 600/547 |
| 5,333,618 A * | 8/1994 | Lekhtman et al. | .......... | 600/547 |
| 5,389,101 A * | 2/1995 | Heilbrun et al. | ............. | 606/130 |
| 5,485,848 A * | 1/1996 | Jackson et al. | .............. | 600/485 |
| 5,540,235 A * | 7/1996 | Wilson | ........................ | 600/554 |
| 5,851,191 A * | 12/1998 | Gozani | ........................ | 600/554 |
| 5,865,761 A * | 2/1999 | Inukai et al. | ................ | 600/513 |
| 6,174,290 B1* | 1/2001 | Cho | ............................ | 600/551 |

FOREIGN PATENT DOCUMENTS

DE   19715421   * 11/1997

* cited by examiner

*Primary Examiner*—Max F. Hindenburg
*Assistant Examiner*—Michael Apanius
(74) *Attorney, Agent, or Firm*—Boyle Fredrickson Newholm Stein & Gratz S.C.

(57) ABSTRACT

An apparatus for and method of conducting a nerve conduction study is provided. In response to predetermined stimulation from an excitation device, a signal is generated that travels through a human body. The apparatus includes a sensing electrode operatively engagable with the human body downstream of the excitation device for sensing the signal. The apparatus further includes a pressure mounting structure operatively connected to the sensing electrode for controlling the pressure at which the sensing electrode engages the body. The pressure mounting structure includes a pressure source and a pressure sensor. A controller receives a pressure signal from the pressure sensor and the signal from the sensor electrode. The controller includes software to normalize the amplitude of the signal based on the pressure at which the sensing electrode engages the body.

21 Claims, 4 Drawing Sheets

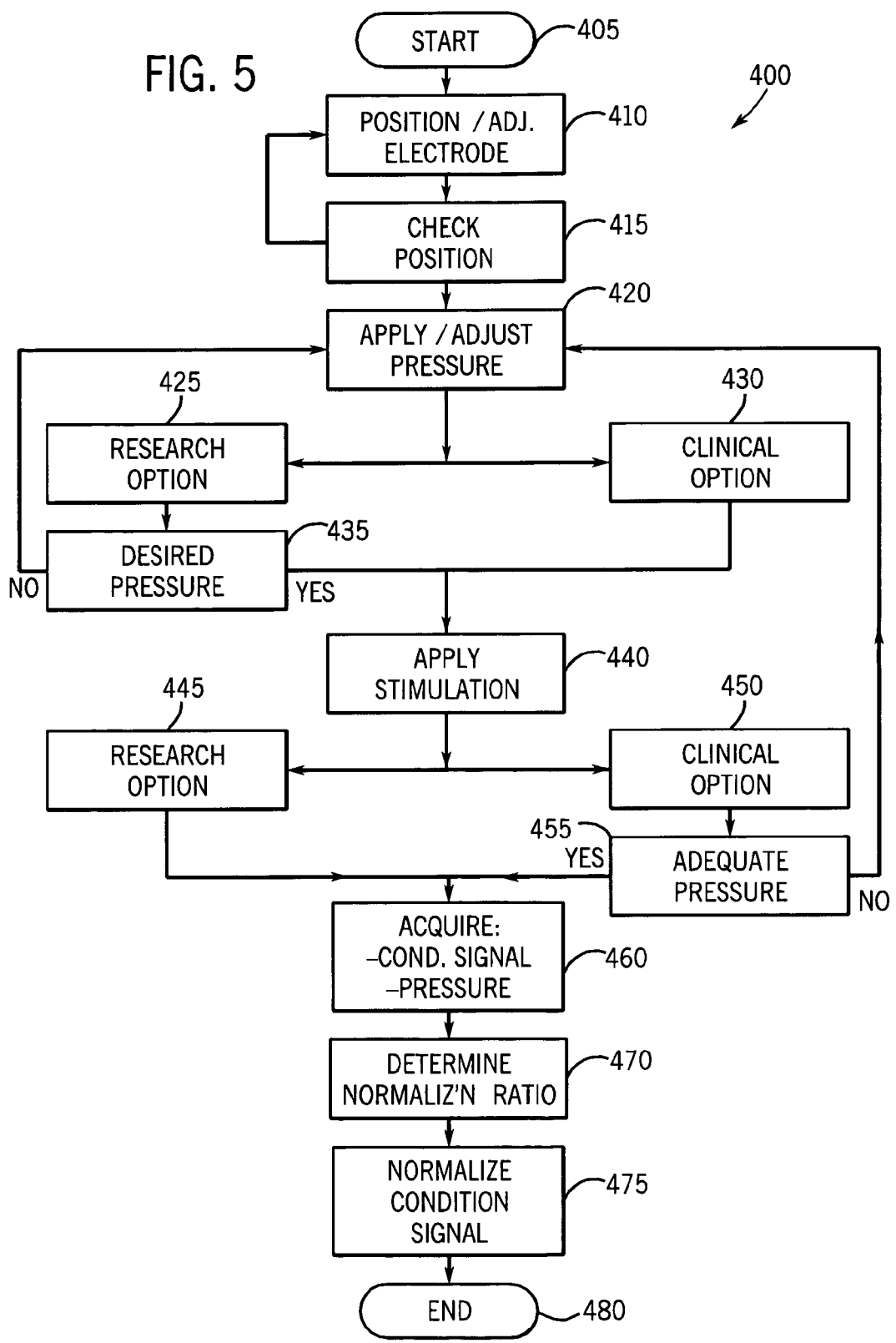

APPARATUS AND METHOD FOR ANALYZING NERVE CONDUCTION

REFERENCE TO GOVERNMENT GRANT

This invention was made with United States government support awarded by the following agencies: NSF 144 KR91. The United States has certain rights in this invention.

FIELD OF THE INVENTION

The invention relates generally to conduction analysis of a selected muscle or nerve, and in particular, to an apparatus for and method of studying an amplitude of a conduction signal generated by a selected muscle or nerve in response to electrical stimulation.

BACKGROUND OF THE INVENTION

Doctors often encounter patients having problems with a particular muscle or nerve (e.g., pinched nerve in the back or neck). Typically, a doctor examines the health of the problematic muscle or nerve by performing an electromyogram (EMG) test. An EMG test generally includes two parts, a nerve conduction study and a needle examination.

The nerve conduction study generally relies on the premise that a nerve is something like an electrical wire. To see if the wire is functioning properly, one delivers an electrical current and evaluates the conductibility of the wire. Analogously, the nerve conduction study includes delivering an electrical current to a selected nerve or muscle and analyzing the nerve's conductibility. How well the selected nerve or muscle conducts the electrical current provides an indication of the health of the nerve or muscle. The physician generally performs the nerve conduction study by attaching a recording or sensing electrode to the surface of the skin of the patient and delivering the electrical current with a pair of electrodes. With delivery of the electrical current, the sensing electrode acquires response signals, referred to as compound motor action potential (CMAP) signals from the selected nerve or muscle. The amplitude of the acquired CMAP signal indicates how many nerve or muscle cells are firing together, and the velocity of the acquired CMAP signal gives an indication of the type of fibers firing. Even though amplitude information is an important parameter in evaluating the functional performance of a nerve or muscle, physicians generally rely only on the conduction velocity to evaluate the performance of the nerve. Physicians do not rely upon amplitude because it has a high level of variance and lesser degree of reproducibility.

Therefore, it is a primary object and feature of the present invention to provide an apparatus for enhancing evaluation of the functional performance of a selected nerve or muscle based on a nerve conduction study.

It is a further object and feature of the present invention to provide an apparatus for and method of studying the effect of pressure on a sensing electrode in regard to the amplitude level of a conduction signal acquired during a nerve conduction study.

SUMMARY OF THE INVENTION

In accordance with the present invention, an apparatus and a method is provided to perform a nerve conduction study that enhances evaluation of the functional performance of a nerve or muscle. The present invention shows how an amount of applied pressure on the sensing electrode directly affects the amplitude of the recorded CMAP signal. The apparatus provides known levels of force or pressure on the sensing electrode, and acquires test information used in calibrating the amplitude of the acquired CMAP signal. The calibrated amplitude information enhances accuracy and precision in the evaluation of the functional performance of the selected nerve or muscle.

In one embodiment, the invention provides an apparatus for sensing the amplitude of a signal generated in response to electrical stimulation from an excitation device operatively engaging a human body. The apparatus includes a sensing electrode operatively engagable with the human body downstream of the excitation device for sensing the signal generated in response to electrical stimulation by the excitation device. The apparatus further includes a pressure mounting structure operatively connected to the sensing electrode for controlling the pressure at which the sensing electrode engages the body. The pressure mounting structure may include a pressure source operatively connected to the sensing electrode for applying the pressure at which the sensing electrode engages the body. The pressure mounting structure may further include a pressure electrode that generates a pressure signal representative of the value of the pressure at which the sensing electrode engages the body.

The apparatus may further include a controller electrically connected to receive the pressure signal from the pressure electrode and the signal from the sensing electrode. The controller is configured to perform the steps of determining a pressure normalization ratio from pressure signals acquired from the pressure sensor, and normalizing the acquired conduction signal from the sensing electrode based on the pressure normalization ratio.

In another embodiment, the invention provides for a method for sensing the amplitude of a signal traveling through a human body, the signal generated in response to electrical stimulation from an excitation device operatively engaging the body. The method includes the steps of acquiring the signal from the sensing electrode, exerting a pressure on the sensing electrode, acquiring a pressure signal representative of the pressure at which the sensing electrode engages the body, determining a pressure normalization ratio based on the acquired pressure signal, and normalizing the signal based on the pressure normalization ratio.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

FIG. 5 is a flow diagram of a first embodiment of a method of nerve conduction study in accordance with the present invention.

DETAILED DESCRIPTION

Figure 1:
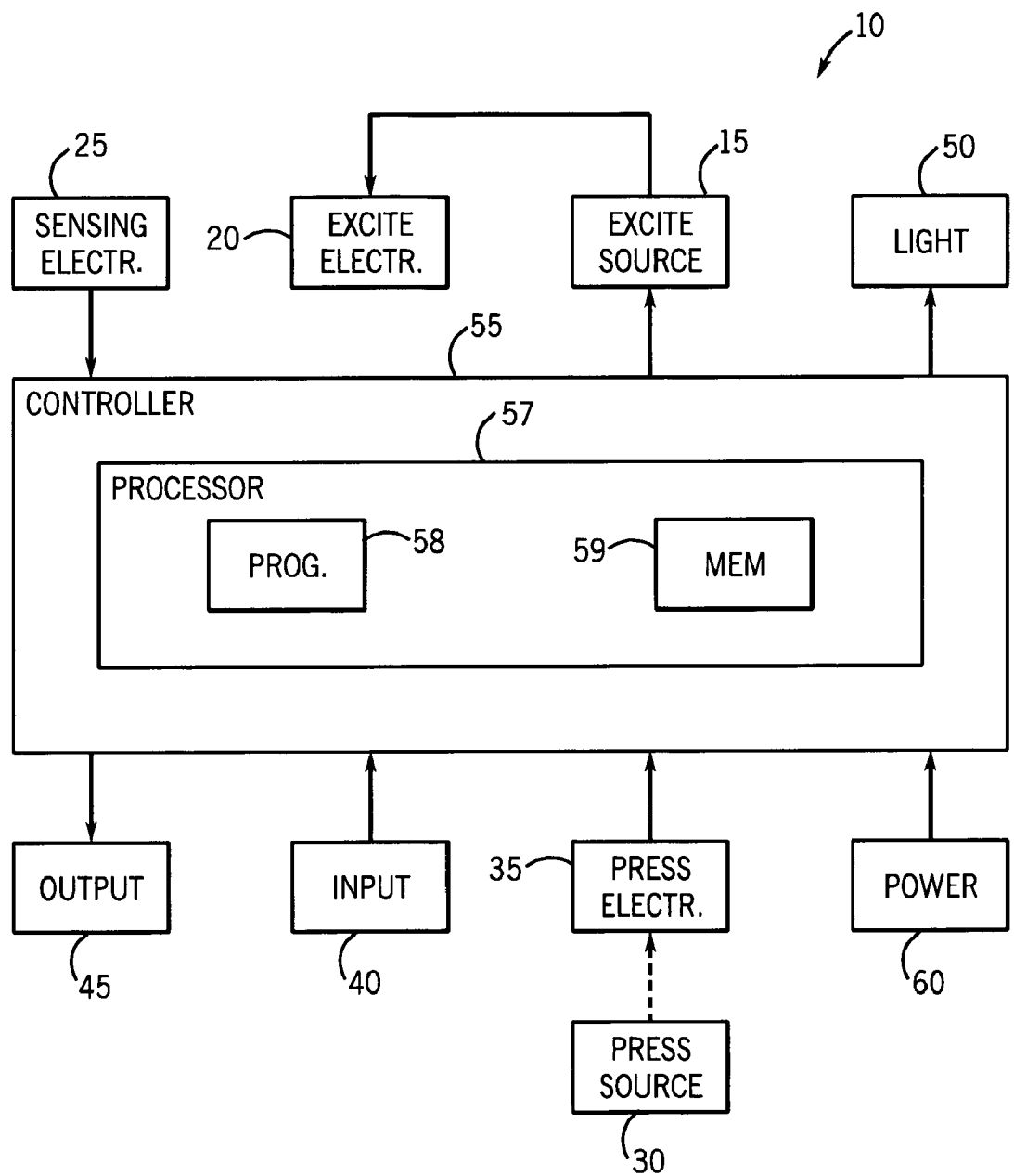
FIG. 1 is a schematic representation of a first embodiment of an apparatus to study nerve conduction in accordance with the present invention.

FIG. 1 is a schematic representation of a first embodiment of an apparatus 10 in accordance with the present invention. The apparatus 10 generally includes an excitation source 15, an excitation electrode 20, a sensing electrode 25, a pressure source 30, a pressure sensor 35, an input device 40, an output device 45, a light source 50, and a controller 55. The following description of the present invention refers to a physician performing a nerve conduction study on a selected nerve located in a hand of a patient. Yet, the operators (e.g., researchers, technicians, etc.) of the apparatus 10 can vary. Likewise, the selected nerve can vary. Furthermore, the present invention can be used to study other nerves as well as miscellaneous muscles.

The excitation source 15 provides electrical current to the excitation electrode 20 positioned on the patient. One embodiment of the excitation source 15 is a current generator electrically connected to the excitation electrode 20. The physician touches the skin surface of the patient with the electrode 20 at a position to deliver the electrical current to the selected nerve. An electrical ground is typically connected to the patient to complete the current path. The type of excitation source 15 and/or excitation electrode 20 and the level/duration of electrical current can vary. The physician delivers the electrical current to the patient at a location to generate a response from the selected nerve. The nerve reacts to the electrical current by providing a conduction signal, referred to as a compound motor action potential (CMAP) signal. The CMAP signal provides a recordable reaction that reflects the performance function of the selected nerve.

The physician positions the sensing electrode 25 at the skin surface to acquire the CMAP signal response from the selected nerve. The type and location of the sensing electrode 25 can vary. The sensing electrode 25 provides the CMAP signal to the controller 55 for processing. The CMAP signal generally includes a velocity and an amplitude level.

The pressure source 30 applies a measurable force normal to the sensing electrode 25 acquiring the CMAP signal. One embodiment of the pressure source 30 includes a micrometer. The pressure sensor 35 provides a pressure signal representative of a value of the applied pressure by the pressure source 30 to the controller 55. One embodiment of the pressure sensor 35 includes a load cell (discussed later) positioned between the pressure source 30 and the sensing electrode 25. An exemplary load cell is manufactured by ENTRAN®. The types of pressure sources 30 (e.g., hands, vises, etc.) and pressure sensors 35 (e.g., strain gauges, etc.) can vary.

The input device 40 is configured to provide input information to the controller 55. The input information can include the type of sensing electrode 25, the selected nerve or muscle under study, patient biography, etc. The types of input devices 40 (e.g., keyboards, touch-screen panels, switches, push-buttons, etc.) can vary. The output device 45 is configured to display output information from the controller 55 for viewing by the physician. The output device 45 can provide a display of a pressure reading from the pressure electrode, an acquired CMAP waveform, an amplitude level and velocity of the CMAP waveform, etc. The type of output device 45 (e.g., display screen, monitor, LCDs, etc.) can also vary.

The light source 50 illuminates over the general area of the skin surface receiving the sensing electrode 25. One embodiment of the light source 50 illuminates a grid 56 configured to provide a reference for placement of the sensing electrode 25. The type, of reference (e.g., bulls eye, etc.), color, activation (e.g., manual, automatic, etc.), and position of the light source 50 can vary. The illumination of the grid 56 provides a reference for placing the sensing electrode 25 at the same position on the body.

The controller 55 is electrically connected to the excitation source 15, the sensing electrode 25, the pressure sensor 35, the input device 40, the output device 45, and the light source 50. One embodiment of the controller 55 includes a processor 57 configured by one or more modules of software to operate the apparatus. The processor 57 includes a program storage 58 and a memory storage 59. The program storage 58 contains the one or modules of software that configure the processor 57. The memory storage 59 provides for storage of data received by the controller 55 (e.g., pressure readings, CMAP signals, etc.).

A power supply 60 provides electrical power to the apparatus 10. In one embodiment, the power supply 60 supplies power to the excitation source 15, the pressure sensor 35, the input 40 and output 45 devices, the light source 50, and the controller 55. In other embodiments of the apparatus 10, one or more of the above elements can have its own power supply.

Figure 2:
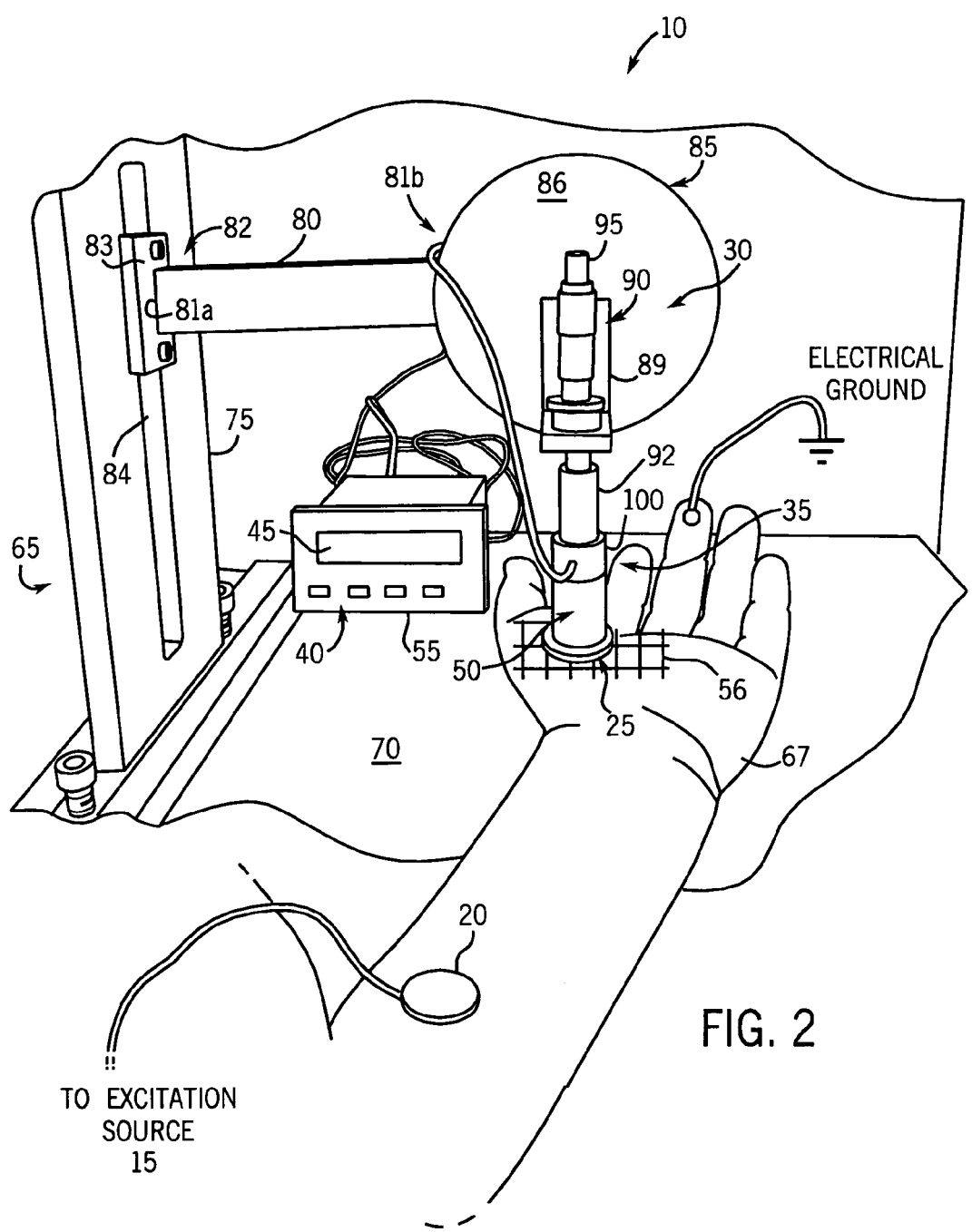
FIG. 2 is a schematic diagram of the apparatus of FIG. 1 having a platform in accordance with the present invention.

FIG. 2 shows a first embodiment of the apparatus 10 having a pressure mounting structure 65. The pressure mounting structure 65 is operatively connected to the sensing electrode 25 for controlling the pressure at which the sensing electrode 25 engages the hand 67 of the patient. In addition, it is intended that pressure mounting structure 65 orient the sensing electrode 25 at a user selected location on the hand 67, as hereinafter described. Of course, other embodiments of the apparatus 10 and pressure mounting structure 65 can be configured to analyze other miscellaneous nerves or muscles on feet, arms, legs, etc.

The pressure mounting structure 65 includes a platform 70 attached to or mounted with a vertical support 75. The platform 70 includes a flat, rigid surface that can be part of a support stand or a separate panel component. The vertical support 75 is a rigid structure mounted to the platform 70 by a pair of fasteners (e.g., bolts and nuts, screws, spot-weld, etc.). The vertical support 75 and/or platform 70 are configured to provide support for receiving and bearing against the hand 67 of the patient. The pressure mounting structure 65 further includes a horizontal support 80 having a first end 81a attached normal relative to the vertical support 75, and an opposite second end 81b. A vertical adjuster 82 is mounted to second end 81b of horizontal support 80 and is configured to variably adjust the vertical position of the horizontal support 80 and attached pressure source 30, pressure sensor 35, and sensing electrode 25 relative to the hand 67 positioned on the platform 70. The vertical adjuster 82 includes a slide 83 moveable along a channel 84 vertically extending along the vertical support 75. The adjuster 82 is attached by a pair of fasteners (e.g., bolt and nut, screw, spot-weld, etc.) to the horizontal support 80. The type vertical hold (e.g., tightening screw, pinch against channel, etc.) to maintain the position of the adjuster 82 and attached horizontal support 80 can vary.

The pressure mounting structure 65 further includes an angle positioning device operatively connected to the second end 81b of horizontal support 80 for controlling an angle at which the sensing electrode 25 engages the hand. In the depicted embodiment, the angle positioning device includes a dial 85 rotatably mounted to the second end 81b of the horizontal support 80. The dial 85 is in pivotal support of the pressure source 30 and sensing electrode 25. The dial 85 is configured to position the sensing electrode 25, the pressure source 30, and the pressure electrode 35 at various desired rotational angles for engaging the hand 67 of the patient. The dial 85 includes a disc 86 attached at the center by a hinge 87 to the second end 81b of the horizontal support 80. A bracket 89 attached to the disc 86 supports the pressure source 30. The type of fastener and/or bracket 89 can vary. The composition (e.g., wood, plastic, metal, etc.) of the above-described elements of the support structure 65 can vary. The type of angular position holder (e.g., tightening screw, friction, etc.) to maintain the angular position of the disc 86 and to attach disc 86 relative to the platform 70 can vary. The horizontal support 80 and dial 85 are configured to allow the pressure source 30, pressure sensor 35, and sensing electrode 25 to engage various locations of the patient's hand 67 at various positions against the platform 70 and/or vertical support 75.

As shown in FIG. 2, the pressure source 30 includes a micrometer 90 having one end 92 configured to bias the sensing electrode 25 against a hand 67 supported against the platform 70. The other end of the micrometer 90 includes an adjustment knob 95. The physician can slide the vertical adjustment 82 and horizontal support 80 and rotate the dial 85 to change position of the micrometer 90 so as to provide a controlled application of pressure to the sensing electrode 25.

Pressure sensor 35 may include a load cell 100 positioned between the first end 92 of the micrometer 90 and the sensing electrode 25. The load cell 100 can have its own power supply or receive electrical power from the controller 55. The load cell 100 provides the pressure signal to the controller 55. Light source 50 is disposed between the load cell and the sensing electrode 25. Alternatively, the light source 50 can be positioned at other locations (e.g., underneath the hand, designated support, etc.). The sensing electrode 25 is attached to the apparatus 10. Alternatively, the sensing electrode 25 can be individually positioned on the patient's hand 67 separate from the remaining elements of the apparatus 10.

The controller 55 controls activation of the light source 50. For example, the controller 55 may provide a signal that activates the light source upon detecting the sensing electrode 25 making contact with the hand 67. Alternatively, the controller 55 may provide the electrical power to the light source based on a manual/automatic switch disposed at the controller or at the light source itself.

The controller 55 is also electrically connected to the sensing electrode 25 and the load cell 100. The excitation source 15 is shown separated from the controller 55. Of course, another embodiment of the apparatus 10 can include the excitation source 15 adjacent the controller 55 in a housing. An electrical ground is attached to the arm of the patient to complete the electrical circuit with the excitation source 15 and electrode 20.

Figure 3:
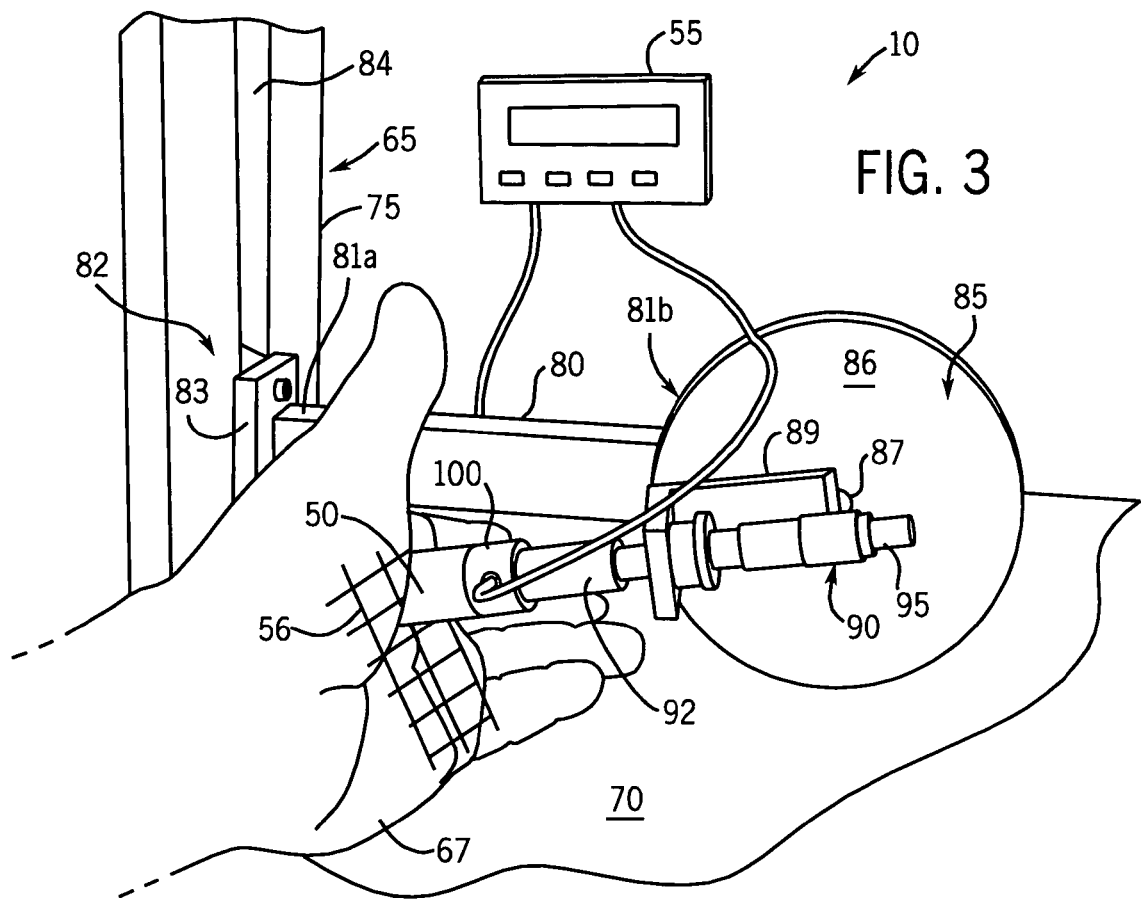
FIG. 3 is a schematic diagram of the apparatus of FIG. 2 rotated to a changed position.

FIG. 3 shows another illustration of the apparatus 10 at a rotated position relative to the patient's hand 67 supported against the vertical support 75 and platform 70 of the apparatus 10. The dial 85 is configured to position the micrometer 90, load cell 100, light source 50, and sensing electrode 25 in various rotational positions to properly apply normal pressure to and acquire an adequate conduction signal from the sensing electrode 25 positioned on the hand 67 of the patient.

Figure 4:
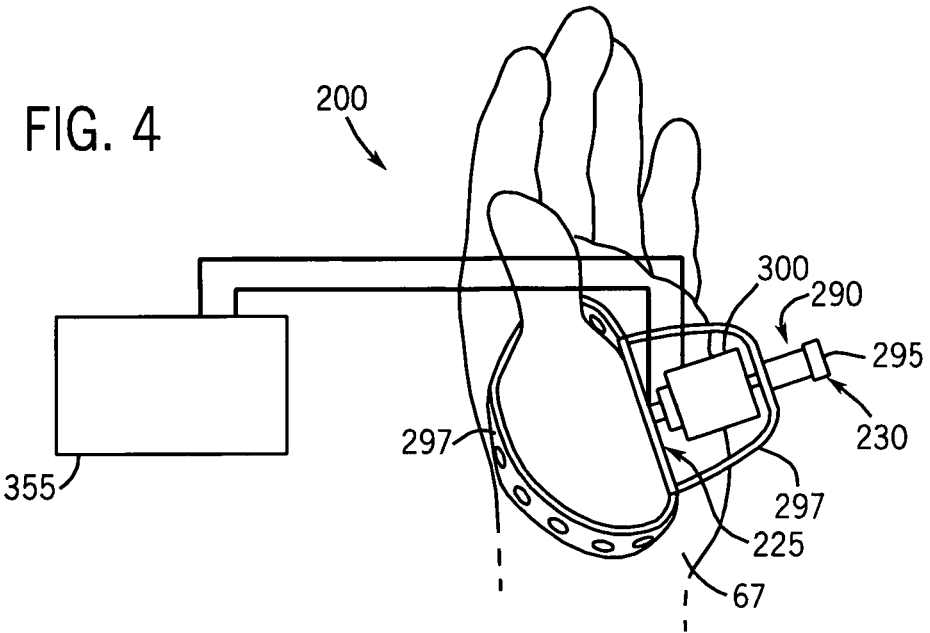
FIG. 4 is a schematic diagram of an alternative embodiment of an apparatus to study nerve conduction in accordance with the present invention.

FIG. 4 shows yet another embodiment of an apparatus 200 for performing a nerve conduction study on a patient. The apparatus 200 includes a sensing electrode 225 configured to acquire a conduction signal from the hand 67. The apparatus 200 also includes a pressure source 230 having a micrometer 290 and an adjustment knob 295 coupled with a strap 297. The adjustment knob 295 is configured to change the tension of a strap 297 wrapped around at least a portion of the hand 67, thereby applying a controlled pressure to the sensing electrode 225. By increasing the tension of the strap 297, the physician can controllably increase the application of pressure applied by the micrometer 290 against the sensing electrode 225. A load cell 300 acquires a reading of the applied pressure by the pressure source 230. The type of pressure source 230 (e.g., human, vise, etc.) and strap 297 (e.g., perforated, belt, etc.) can vary. A controller 355 is electrically connected to receive signals from the sensing electrode 225 and the load cell 300 similar to the apparatus described in FIG. 2.

Other embodiments of the apparatus 10 and 200 may include elements having individual displays, controls, and power supplies.

Having described the basic architecture of several embodiments of the apparatus 10 of the present invention, a method 400 of operation of the apparatus 10 will now be described as shown in FIG. 5. It is envisioned that the method 400 of operation can be modified for other embodiments of the apparatus 10. Furthermore, it is envisioned that not all the acts may be required, that some of the acts may be modified, or that the order of the acts may vary.

As shown in FIG. 5 and at act 405, a physician activates or starts the apparatus 10. The patient positions a hand 67 on the apparatus 10 for nerve conduction study. The light source 50 can illuminate the grid 56 to provide a reference for positioning the sensing electrode 25 at the same location on the hand. At act 410, a physician positions the excitation electrode 20 and the sensing electrode 25 on the patient. In one embodiment, the physician positions an excitation electrode 20 at or near the elbow of the patient. The physician positions the sensing electrode 25 near a selected nerve in the patient's hand 67. The excitation electrode 20 is connected to the excitation source 15. A second electrode positioned on the patient is connected to electrical ground. At act 415, the physician determines whether the position of the sensing electrode 25 should be adjusted to more adequately acquire a CMAP signal from the selected nerve. At act 420, the physician applies pressure to the sensing electrode 25. In one embodiment and as shown in FIG. 2, the physician applies pressure by adjusting the extended position of the micrometer 90 biased against the sensing electrode 25 and the hand 67 of the patient. The change in extended position of the micrometer 90 applies additional pressure on the sensing electrode 25. The apparatus 10 is configured to provide repeatable degrees of pressure to the sensing electrode 25.

The physician has a choice to select a research option (act 425) or clinical option (act 430) for performing the nerve conduction study. The research option is configured to study the general effect of variable pressure on the conduction signal acquired by the sensing electrode 25. The clinical option is generally configured to perform a nerve conduction study of a selected nerve of a patient. If the research option (act 425) is selected, the physician determines whether the desired pressure is placed on the sensing electrode 25 (act 435). If not, then the physician adjusts the application of pressure by the pressure source 30 (act 420).

At act 440, the physician applies electrical stimulation, or delivers the electrical current, to the excitation electrode 20. Again, the physician can select a research option (act 445) or a clinical option (act 450). If the physician selects the clinical option (act 450), then the physician determines whether the pressure source 30 is applying adequate pressure to the sensing electrode 25. Inadequate pressure on the sensing electrode 25 can reduce the clarity at the conduction signal (act 455). If the pressure is inadequate then the physician adjusts the pressure applied by the pressure source 30 to the sensing electrode 25 (act 420).

At act 460, the controller 55 acquires the pressure signal from the pressure sensor 35 and the conduction signal from the sensing electrode 25. At act 470, the controller 55 determines a pressure normalization ratio. In one embodiment, determining the pressure normalization ratio is determined during calibration of the apparatus 10. The act of determining the pressure normalization ratio includes the physician determining a change in the amplitude level of the acquired conduction signal caused by a known application of pressure by the pressure source 30 to the sensing electrode 25. In one embodiment, the pressure normalization ratio is based on a linear relationship. Thereby, the pressure normalization ratio equals the gradient (e.g., change in amplitude/0.1 lb. change in pressure) of a straight line representing the change in amplitude of the conduction signal caused by a known application of pressure on the sensing electrode 25. In another embodiment, a non-linear relationship can be used to determine the pressure normalization ratio. If based on a non-linear relationship, a physician can use a look-up table of tangential values representing the change in amplitude of the conduction signal for a known application of pressure by the pressure source 30 to the sensing electrode 25.

At act 475, the controller normalizes the conduction signal with respect to the pressure normalization ratio. In one embodiment, normalizing the conduction signal includes multiplying the acquired conduction signal by the pressure normalization ratio. Act 480 is the end of operation of the apparatus 10.

By normalizing the effect of pressure on the amplitude of the nerve conduction signal, a physician can place more confidence in the accuracy of the measured amplitude values of the acquired conduction signal. This acquired amplitude information provides performance information in addition to the measured velocity of the nerve conduction signal. While conduction velocity provides information regarding the state of the nerve conduction pathways, the amplitude of the nerve conduction signal provides insight about the health of nerve cells in the area. Thereby, the present invention provides the physician with an apparatus of and a method for studying and acquiring amplitude information of nerve conduction studies that enable a more thorough evaluation of the performance of a studied nerve or muscle.

The apparatus 10 and the method 400 can be used to perform tests in nerve conduction performed to evaluate for anterior horn disease, root lesions related to compressed spinal nerve roots, plexus lesions, compression/entrapment neuropathies, distal myopathies, neuromuscular transmission defects, polyneuropathies, trauma, etc. These disfunctions/diseases can be associated with various nerves or muscles located in various areas of the body (e.g., foot, leg, hand, spine, etc.). For example, a nerve conduction study may be performed to evaluate nerve damage above and below a trauma to the knee, including nerves in the foot. The apparatus 10 is configured to support the various areas of the foot in providing a repeatable pressure to a sensing electrode for acquiring conduction signal data generated by the selected nerve(s) in the foot.

Various modes of carrying out the invention are contemplated as being within the scope of the following claim particularly pointing out and distinctly claiming the subject matter, which is regarded as the invention.

I claim:

1. An apparatus for sensing the amplitude of a signal traveling through a body, comprising:
   an excitation device operatively engageable with the body, the excitation device generating the signal that travels along a nerve in the body;
   sensing electrode operatively engagable with the body under a pressure downstream of the excitation device for sensing the signal generated by the excitation device and traveling along the nerve in the body;
   a pressure mounting structure operatively connected to the sensing electrode for controlling the pressure at which the sensing electrode engages the body;
   a pressure sensor disposed adjacent the sensing electrode, the pressure sensor generating a pressure signal corresponding to the pressure at which the sensing electrode engages the body; and
   a controller electrically connected to the pressure sensor for receiving the pressure signal and to the sensing electrode for receiving the signal sensed by the sensing electrode and performing the step of:
   determining a pressure normalization ratio in response to the pressure signal acquired from the pressure sensor; and
   normalizing the acquired signal from the sensing electrode based on the pressure normalization ratio.

2. The apparatus of claim 1 wherein the pressure mounting structure includes a pressure source operatively connected to the sensing electrode for applying the pressure at which the sensing electrode engages the body.

3. The apparatus of claim 2 wherein the pressure source includes a micrometer configured to adjust the pressure at which the sensing electrode engages the body.

4. The apparatus of claim 1 wherein the pressure sensor includes a load cell.

5. The apparatus of claim 1 wherein the controller performs the step of:
   displaying a pressure value representative of the pressure at which the sensing electrode engages the body.

6. The apparatus of claim 1 further comprising a positioning structure operatively connected to the sensing electrode for positioning the sensing electrode at a user selected location adjacent the body.

7. The apparatus of claim 6 wherein the positioning structure includes a vertical positioning device, the vertical positioning device allowing a user to adjust the vertical position of the sensing electrode relative to the body.

8. The apparatus of claim 6 wherein the positioning structure includes a dial configured to rotate the sensing electrode about a horizontal axis so as to allow a user to control an angle at which the sensing electrode engages the body.

9. The apparatus of claim 6 wherein the positioning structure includes a light source configured to illuminate a grid on the body to facilitate the positioning of the sensing electrode on the body.

10. The apparatus of claim 1 wherein the pressure mounting structure includes a strap operatively connected to the pressure sensor and sensing electrode for holding the sensing electrode against the body.

11. An apparatus for sensing a signal traveling through a body, comprising:
   an excitation source operatively engageable with the body, the excitation source generating the signal that travels along a nerve in the body;

a sensing electrode operatively engagable with the body downstream of the excitation source for sensing the signal generated by the excitation source and traveling along the nerve in the body;

a pressure source configured to provide a pressure at which the sensing electrode engages the body;

a pressure sensor coupled between the pressure source and the sensing electrode, the pressure sensor generating a pressure signal representative of the pressure at which the sensing electrode engages the body; and a controller electrically connected to the pressure sensor and to the sensing electrode, the controller:

acquiring the pressure signal from the pressure sensor and the signal from the sensing electrode;

determining a pressure normalization ratio in response to the pressure signal; and normalizing the signal from the sensing electrode based on the pressure normalization ratio.

12. The apparatus of claim 11 wherein the pressure source includes a micrometer configured to selectively control the pressure at which the sensing electrode engages the body.

13. The apparatus of claim 11 wherein the pressure sensor includes a load cell.

14. The apparatus of claim 11 further comprising a light source configured to illuminate a grid on the body, the grid providing a guide for positioning the sensing electrode on the body.

15. The apparatus of claim 11 further comprising a pressure mounting structure operatively connected to the pressure source for orientating the pressure along an axis normal to the body.

16. The apparatus of claim 15 wherein the pressure mounting structure includes a strap that holds the pressure sensor and sensing electrode against the body.

17. The apparatus of claim 16 wherein the strap is configured with a micrometer for changing tension in the strap and providing the pressure at which the sensing electrode engages the body.

18. A method for sensing a signal traveling through a body, the method comprising the steps of:

generating the signal with an excitation device such that the signal travels along a nerve in the body;

positioning a sensing electrode on the body;

exerting a pressure on the sensing electrode against the body;

receiving the signal traveling along the nerve in the body with the sensing electrode;

generating a pressure signal representative of the pressure at which the sensing electrode engages the body;

determining a pressure normalization ratio in response to pressure signal; and normalizing the signal received by the sensing electrode in response to the pressure normalization ratio.

19. The method of claim 18 wherein the pressure exerted on the sensing electrode is normal to the body.

20. The method of claim 18 comprising the additional step of:

measuring the amplitude level of the signal received with the sensing electrode.

21. The method of claim 18 comprising the additional steps of:

repeating the pressure exerted on the sensing electrode against the body;

receiving the signal with the sensing electrode; and measuring the amplitude level of the signal received with the sensing electrode.

* * * * *